(12) United States Patent
Breckenridge

(10) Patent No.: US 6,296,766 B1
(45) Date of Patent: Oct. 2, 2001

(54) ANAEROBIC DIGESTER SYSTEM

(76) Inventor: Leon Breckenridge, 16213 E. 22nd, Veradale, WA (US) 99037

(*) Notice: Subject to any disclaimer, the term of this patent is extended or adjusted under 35 U.S.C. 154(b) by 0 days.

(21) Appl. No.: 09/439,815

(22) Filed: Nov. 12, 1999

(51) Int. Cl.$^7$ ........................................ C02F 3/28
(52) U.S. Cl. .................... 210/613; 71/10; 210/603; 210/614; 706/903
(58) Field of Search ..................... 210/96.1, 143, 210/603, 614, 739, 601, 610, 613, 615; 435/267, 286.1, 289.1; 71/7, 8, 10, 11, 13, 9; 706/15, 903, 914, 932

(56) References Cited

U.S. PATENT DOCUMENTS

| | | |
|---|---|---|
| 3,933,628 | 1/1976 | Varani . |
| 4,100,023 | 7/1978 | McDonald . |
| 4,161,426 | 7/1979 | Kneer . |
| 4,437,987 | 3/1984 | Thornton et al. ............... 210/137 |
| 4,613,433 | 9/1986 | McKeown ....................... 210/150 |
| 4,648,968 | 3/1987 | Cutler ............................ 210/218 |
| 4,710,292 | 12/1987 | DeVos ........................... 210/218 |
| 5,080,786 | 1/1992 | De Lima ........................ 210/218 |
| 5,082,486 | 1/1992 | Glogowski ......................... 71/9 |
| 5,158,593 | 10/1992 | De Lima ........................... 71/9 |
| 5,185,079 | 2/1993 | Dague ............................ 210/603 |
| 5,207,911 | 5/1993 | Pellegrin et al. ............... 210/603 |
| 5,227,051 | 7/1993 | Oshima ......................... 210/137 |
| 5,240,611 | 8/1993 | Burton .......................... 210/603 |
| 5,248,423 | * 9/1993 | Moletta et al. ................ 210/614 |
| 5,282,879 | 2/1994 | Baccarani ........................ 71/10 |
| 5,310,485 | 5/1994 | Roshanravan ................. 210/603 |
| 5,389,258 | 2/1995 | Smis et al. .................... 210/603 |
| 5,393,317 | 2/1995 | Robinson ......................... 71/12 |
| 5,423,895 | 6/1995 | Wight et al. ................... 48/197 |
| 5,451,319 | 9/1995 | Kobayashi .................... 210/603 |
| 5,470,745 | * 11/1995 | Beteau et al. ................. 435/286.1 |
| 5,490,933 | 2/1996 | LaPack et al. ................ 210/603 |
| 5,500,118 | 3/1996 | Coenen et al. ................ 210/603 |
| 5,500,123 | 3/1996 | Srivastava .................... 210/603 |
| 5,500,306 | 3/1996 | Hsu et al. ........................ 429/17 |
| 5,525,228 | 6/1996 | Dague et al. .................. 210/603 |
| 5,525,229 | 6/1996 | Shih .............................. 210/603 |
| 5,527,464 | 6/1996 | Bartha et al. ................. 210/603 |
| 5,529,692 | 6/1996 | Kubler .......................... 210/603 |
| 5,547,578 | * 8/1996 | Nielsen ......................... 210/614 |
| 5,581,459 | * 12/1996 | Enbutsu et al. . |
| 5,589,068 | * 12/1996 | Nielsen ......................... 210/614 |
| 5,597,399 | 1/1997 | Basu et al. ....................... 71/9 |
| 5,601,720 | * 2/1997 | Schmid ......................... 210/614 |
| 5,637,219 | 6/1997 | Robinson et al. ............. 210/603 |
| 5,774,633 | * 6/1998 | Baba et al. . |
| 5,806,903 | * 3/1999 | Lo . |

* cited by examiner

Primary Examiner—Joseph W. Drodge
(74) Attorney, Agent, or Firm—Stratton Ballew PLLC

(57) ABSTRACT

A method for an anaerobic digester system is provided that employs a cumulative data base to better monitor and control the anaerobic process, as compared with conventional anaerobic digester systems. The method includes the storing and ensiling of a feedstock, preferably a biomass, to form a digester feed material, which then processed by a digester. The process evolves a biogas and forms a digested material. The process is monitored, to collect a plurality of digester data from all stages of the process. These individual points or elements of the data are telemetered to a cumulative data base for storage and eventual retrieval and the cumulative data base is mined to compile predictive, feed forward controls and construct feedstock correlations between the metabolic activity within the digesters and an analysis of the feedstocks into the digesters. The method further includes the production of a high quality plant growth media from the digested mash, and recovery of the biogas generated within the digester. The biogas is collected with the aid of a biogas recovery system. The biogas is predominantly methane, and the anaerobic digester system is preferably operated to maximize the quantity and quality of methane generated.

9 Claims, 7 Drawing Sheets

ANAEROBIC DIGESTER SYSTEM

TECHNICAL FIELD

The invention relates to a digester system that utilizes anaerobic microbes to convert organic material into a biogas and a plant growth media on an industrial scale. More specifically, the present invention relates to a process for monitoring, then analyzing and finally, very precisely controlling a multistage digestion process, to optimize operation of the digester system. The process includes an anaerobic digester, and a control system for the digester that employs pattern recognition.

BACKGROUND OF THE INVENTION

The pre-treatment of cattle feed or roughage, before feeding it to cattle, has long been a subject of research. For instance, during the drought years of the 1930's, there was a need to make cattle feed out of weeds and about anything else that was growing. It was then demonstrated that almost any organic material having any potential as fodder could be made into digestible animal feed. The green fodder could be preserved and converted into animal feed within a silo or similar storage. The process of storing and preserving fodder is known as ensiling.

Ensilage is essentially a partially fermented organic material. Most temperate regions of the planet generate large amounts of organic material, commonly called biomass. Most biomass is considered a waste material and typically disposed of as rubbish. Much of this waste material could be converted into a plant growth media and methane ($CH_4$) by first converting it to silage and then processing it through an anaerobic methane producing digester.

The anaerobic digestion process can be fed by an enormous variety of biomass sources. As a result, the process can be used to resolve an equally wide variety of waste disposal problems. If this waste biomass can be efficiently converted into energy, it could be utilized to replace scarce fossil fuels.

Some site specific sources of biomass include:

| Dairy farms | Fruit processors | Mint farms | Cheese plants |
|---|---|---|---|
| Potato processors | Hog farms | Cattle feed lots | Egg farms |
| Poultry farms | Hop farms | Frozen food processors | |

Some examples of particular biomass materials include:

| Wheat straw | Corn silage | Rice Straw | Food wastes |
|---|---|---|---|
| Grass seed straw | Residential yard debris | Selected municipal solid wastes | |

The physical aspects of an anaerobic digester system are essentially a vessel and all of the necessary accessories and other components to create an environment as close as possible to that in which the anaerobe microorganisms naturally live. The initial digestive chambers of bovines are excellent examples of a well functioning anaerobic digester found in nature. The ingestion of grasses or other similar materials by the bovine ultimately produces a manure mash, which is an excellent fertilizer, and produces a methane gas ($CH_4$) emission, as a by-product.

Operating an efficient anaerobic digester roughly patterned after naturally occurring digestive systems, but at an industrial scale, is not a simple task. The feedstocks for such industrial processes are substantially composed of biologically generated material.

A lack of uniform quality of the end product is almost universal in most, if not all, existing industrial scaled anaerobic digesters, and composting operations of a significant scale. This lack in uniformity has led to the dismissal of anaerobic digestion as a viable, reliable methane industrial scale source of methane. To operate even a simple anaerobic digester that substantially mimics the biomass digestive systems found in nature, powerful and sensitive system monitoring methods and controls are needed. This is because in the natural bovine system, hundreds of thousands or even millions of minute and symbiotic organisms have evolved over eons to a self-regulating system.

In the industrial setting, we can observe an example of a high level of sensitivity in the precision of an industrial fermentation process, as typically performed to produce a top quality beer. Typical industrial process control systems use at least one physical parameter, such as pressure, time or temperature for a primary control. When closer control is needed, a second physical parameter is used. Occasionally, a third parameter may also be employed. The use of this "third" parameter or $3^{rd}$ level of control usually results in a process control system with much higher precision than that process's ability to be accurately controlled.

Currently, in most industrial scale anaerobic digesters, the design of various components of the digesters coupled with the control system together allow the temperature to fluctuate anywhere from plus or minus two or three degrees Fahrenheit (F.), up to occasional variations having a range often degrees F., or more. For the digester's anaerobes, even a single degree F change in temperature is at least one hundred times greater than the phenomena that needs to be measured, which is the heat generated by the anaerobes. Therefore, for these conventional industrial digesters, the ten degree "dead band" or noise level of the signal from the phenomena to be measured or controlled, is ten to one hundred times larger than the phenomena's metabolic heat signal that needs to be accurately measured.

A precision control system is of no benefit for these conventional, industrial anaerobic digester systems, because the physical design of the anaerobic digester does not permit "fine tuning" due to the errors produced by the measurement and control system. Therefore, a need exists for both a digester design and a control system for an industrial anaerobic digester, which are better able to monitor and control the anaerobic process.

SUMMARY OF INVENTION

The present invention provides a method for an anaerobic digester system. The method specifically addresses the control difficulties of industrial scale anaerobic digesters, and solves these difficulties by employing a cumulative data base to better monitor and control the anaerobic process, as compared with conventional anaerobic digester systems.

The method of the present invention includes the storing of a feedstock, preferably a biomass, to form a digester feed material. This digester feed material is processed by a digestion process, which mimics the bovine digestion process, in a digester. The process evolves a biogas and forms a digested material. Importantly, the process is monitored, to collect a plurality of digester datum from the digester, and preferably from all stages of the process. These individual points or elements of the datum are telemetered to a cumulative data base for storage and eventual retrieval.

The cumulative data base is "mined" to compile a predictive, feed forward control of an anaerobic digester system. The term mining is employed to describe the process of utilizing an artificially intelligent software application to draw specific relationships from the cumulative data base. This data mining software is a prepackaged and commercially available product, yet highly adaptable to user specific applications. In the present invention, the results of the data mining can be used to construct feedstock correlations between the metabolic activity within the digesters and an analysis of the feedstocks into the digesters. These feedstock correlations can be employed in both feed back and feed forward controls of the anaerobic digester system.

The method of the present invention can further include a recovery of the biogas generated within the digester, with the aid of a biogas recovery system. With the typical biomass feedstock, the biogas formed within the digester is predominantly methane, and the anaerobic digester system is preferably operated to maximize the quantity and quality of methane generated. This biogas formation can be directly related to the metabolic activity within the digesters and optimized with the correlations discovered in the mining of the cumulative data base.

The invention will be better understood by reference to the following detailed description taken in conjunction with the accompanying drawings.

DETAILED DESCRIPTION OF SPECIFIC EMBODIMENTS

The invention provides a method for a digester system that utilizes anaerobic microbes to convert organic material into methane ($CH_4$) and a plant growth media on an industrial scale.

System Overview

Figure 1:
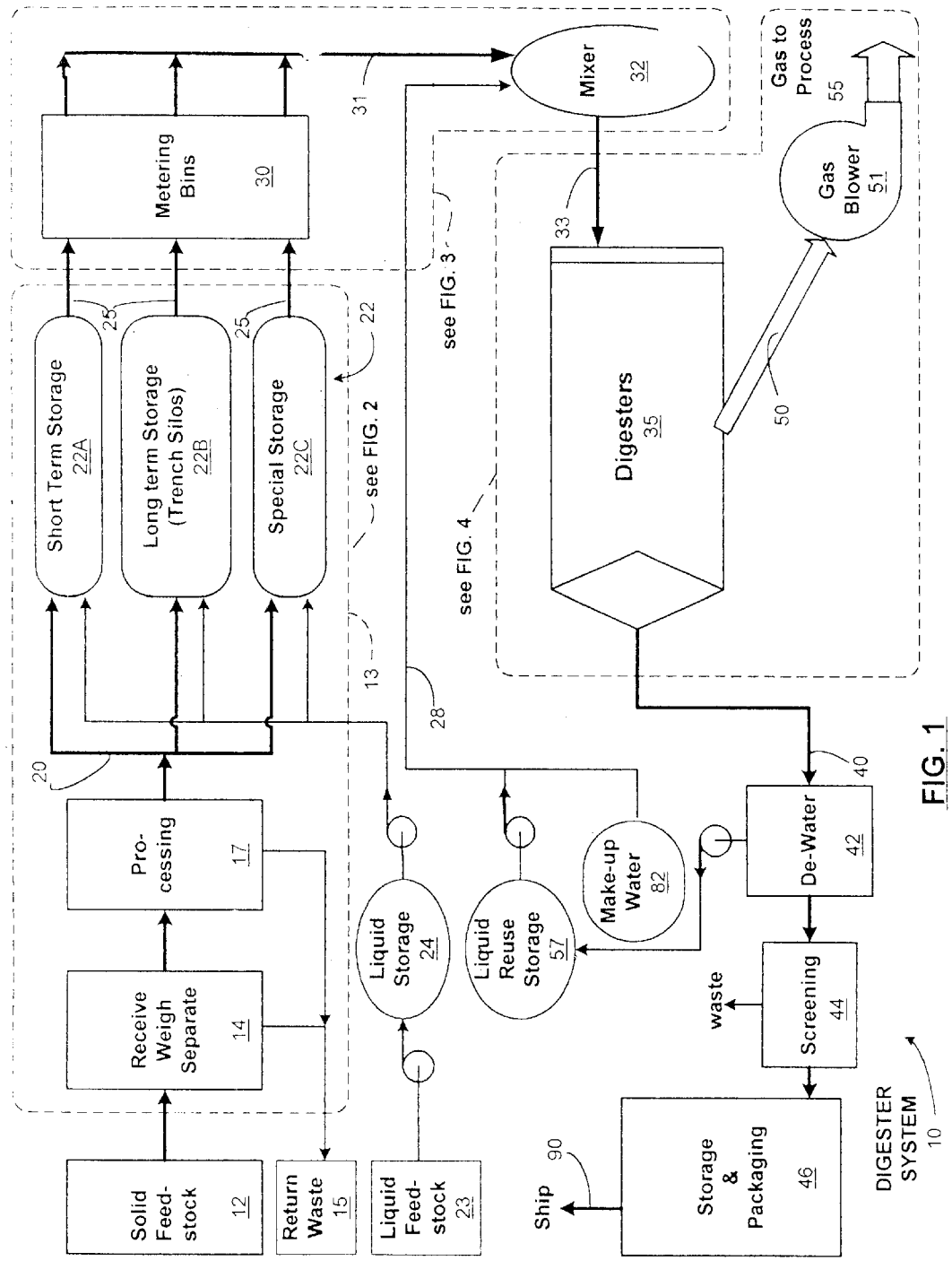
FIG. 1 is a schematic illustration of an overview of an embodiment of the present invention.
Figure 2:
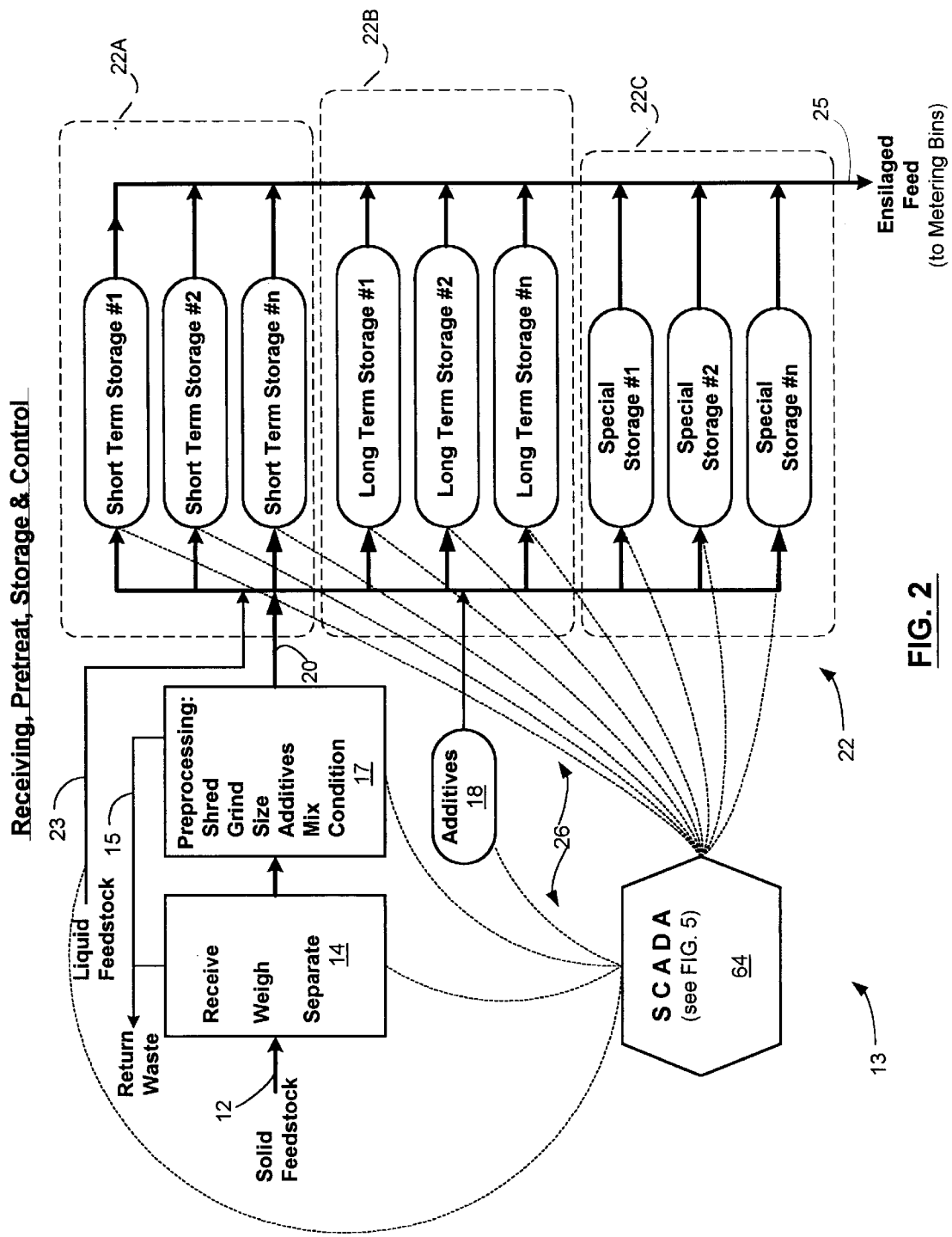
FIG. 2 is a schematic illustration of a receiving, pretreat, storage and control portion of an embodiment of the present invention.

A preferred embodiment of a digester system of the present invention is schematically shown in FIGS. 1 through 7. FIG. 1 shows an overview of the digester system 10. The pre-treatment processing stage of the digester system receives and processes a solid feedstock 12. The pre-treatment process used by the digester system is the process called ensilaging, or making silage. Ensilaging is a first phase of the anaerobic digestion process in which a biomass, or solid feedstock is prepared for a digester 35 by an initial, acidic fermentation by anaerobic microorganisms. The solid feedstock is received into preprocessing and storage components 13. The digester system initially transfers a pre-processed material stream 20 into a storage component 22, which, as detailed in FIG. 2, are preferably a parallel set of trench silos, or a long term storage 22B.

The pre-processed material stream 20 is ensilaged in the trench silos. The process of making and storing of the solid feedstock 12 as a silage also allows the material to be analyzed as a food source for the anaerobes that are currently active within the digesters 35. For a sustainable anaerobic digestion, there are typically more than twenty varieties of anaerobes active at any one time. These microbes can quickly mutate and adapt to flourish in new environmental conditions within a few days.

Figure 3:
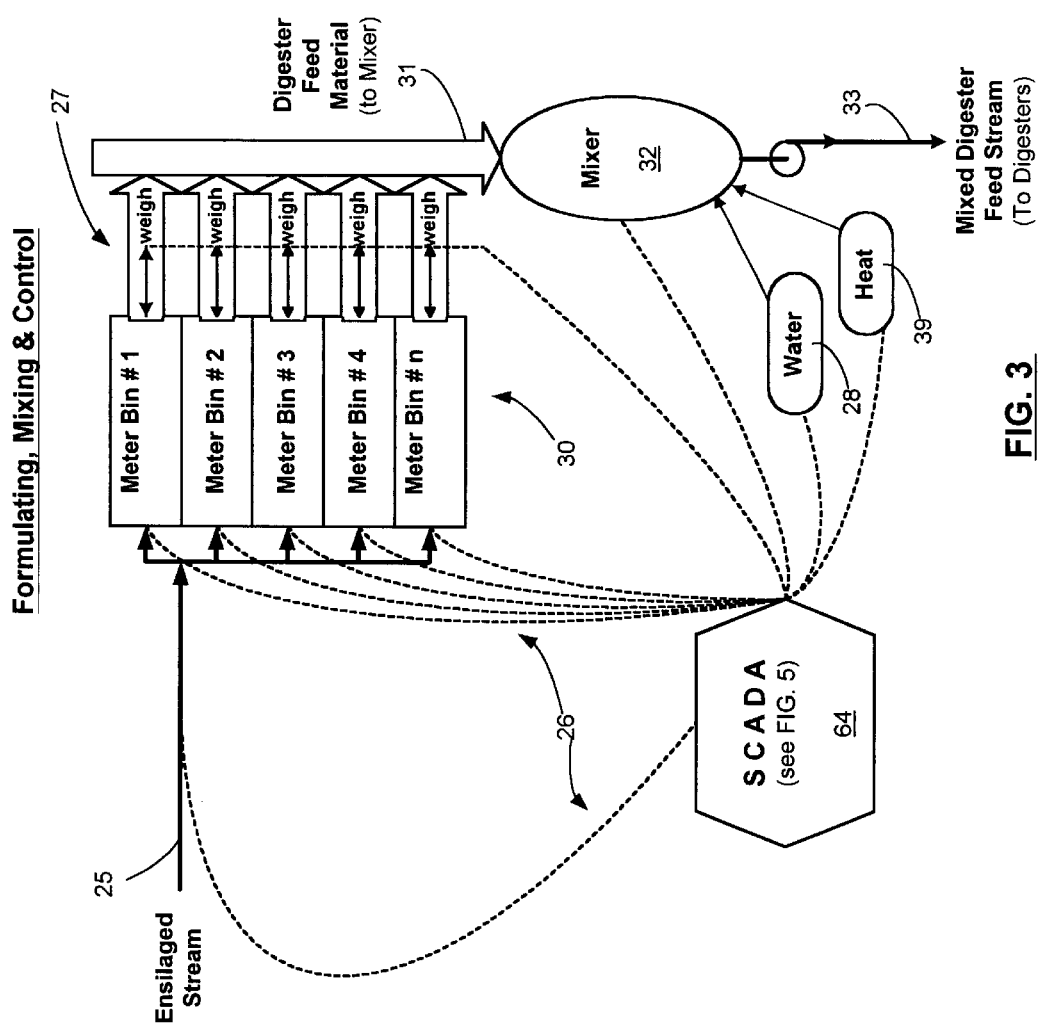
FIG. 3 is a schematic illustration of a formulating, mixing and control portion of an embodiment of the present invention.

As shown in FIG. 1, an ensilaged material stream 25, from the storage 22 is selectively fed into one of the metering bins 30, which are preferably positioned in parallel as shown in FIG. 3. The metering bins measure specific quantities of the ensilaged material to form a digester feed material stream 31. The digester feed material is then introduced into a mixer 32. The digester feed material is thoroughly blended to form a mixed feed stream 33.

Figure 4:
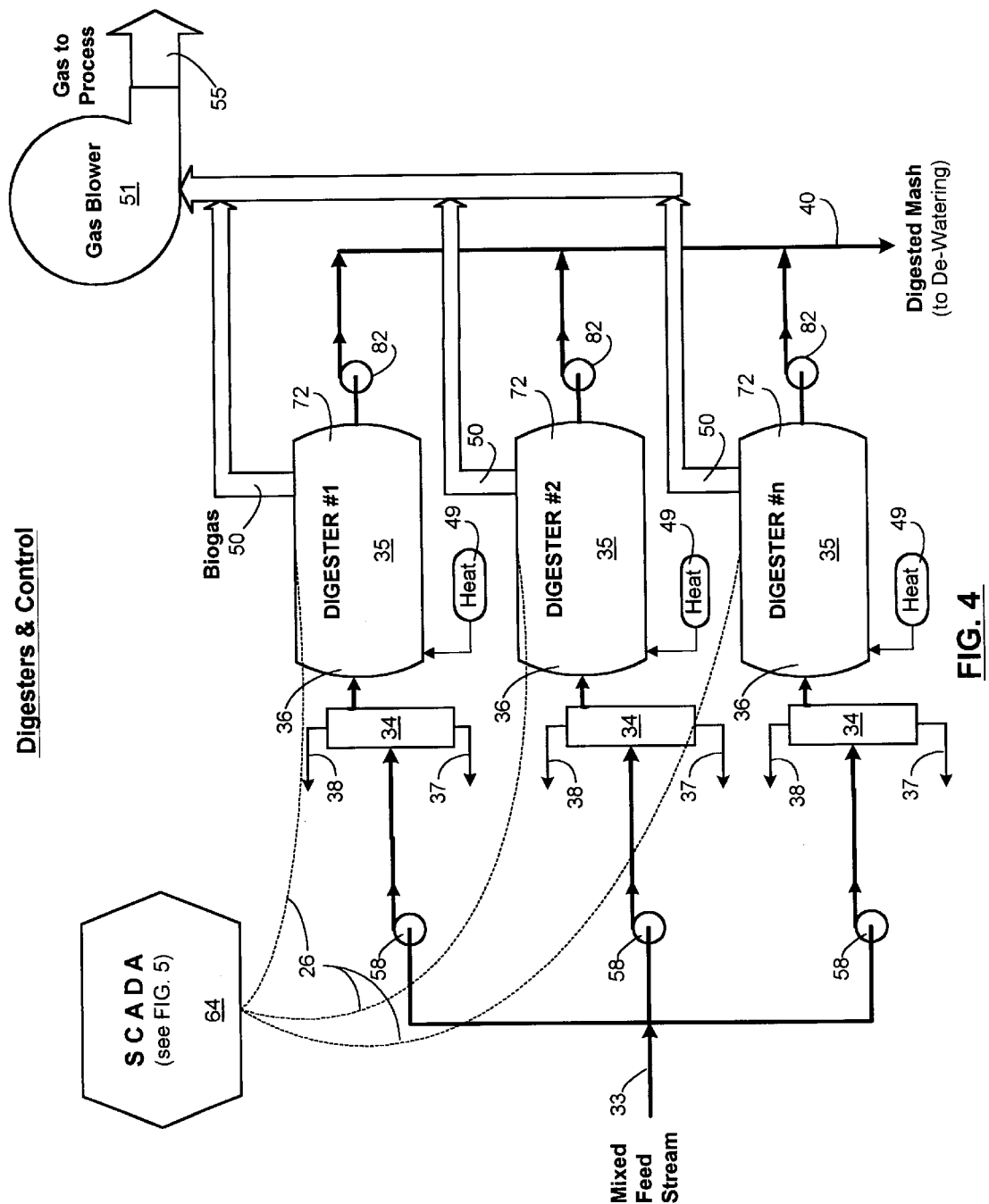
FIG. 4 is a schematic illustration of a digester and control portion of an embodiment of the present invention.

The mixed feed stream 33 is then distributed into a digester 35, which are preferably a parallel set of digesters, as shown in FIG. 4. These energy-efficient methane producing digesters are a central component of the digester system 10 of the present invention. As also shown in FIG. 4, the digesters include a separation section 34, for preprocessing the mixed silage stream. The separation section, which is preferably an integral component of digesters located at the infeed of each digester, cleans heavy inorganic materials from the mixed feed stream. After processing in the digesters, a digested material, or mash stream 40 enters post processing stages that includes a de-water 42 process, a screening 44 and a storage and packaging 46 stage, as shown in FIG. 1.

A primary product of the digester system 10 is a methane gas stream 50, which is produced by the digesters. The gas stream is fed into a gas blower 51 and is immediately available as a gas to process stream 55 for any appropriate process that requires such a gas.

Importantly, the digester system 10 uses advanced information technology capabilities to control the biochemical and physical processes in the system. As shown schematically in FIG. 5, the digester system utilizes a data control system 60 that includes an expert data analysis 62, a cumulative data base 63, and a "supervisory control and data acquisition" (SCADA) system 64.

The expert data analysis 62 utilizes software algorithms that employ a pattern recognition software (PRS) 65, to analyze the data acquired by the SCADA system 64 and generate operational adjustment advisories for system operators. These updated operational adjustments ensure a continually optimal process. In addition, operational data and the results of adjustments are captured and stored in the cumulative database 63. With the cumulative data base, the analytical tools employed in the present invention evolve and reiterate the sum of the data retrieved through the PRS 65 functions, to provide the digester system with increasingly optimal process results over time. Additionally, since naturally occurring anaerobes from cattle are used, we can take advantage of the large amount of existing data on what to feed the anaerobes, to obtain maximum metabolic activity, which for that industry is directly attributable to maximizing weight gain, milk production, and the like.

Receiving Pre-processing, Storage and Control

As shown in FIG. 1, the solid feedstock 12, which preferably consist of mostly organic materials, water and water-soluble components is received at a weigh/separation station 14. Any apparent large and non-digestible materials are removed at this stage and rejected from the process in a stream of return waste 15. The remainder of the solid feedstock can be shredded, ground to size and analyzed to determine if any additives 18 are needed to produce a product, which will meet one of many selected formulas after the mixture has been stored and ensilaged for a minimum amount of time.

Figure 5:
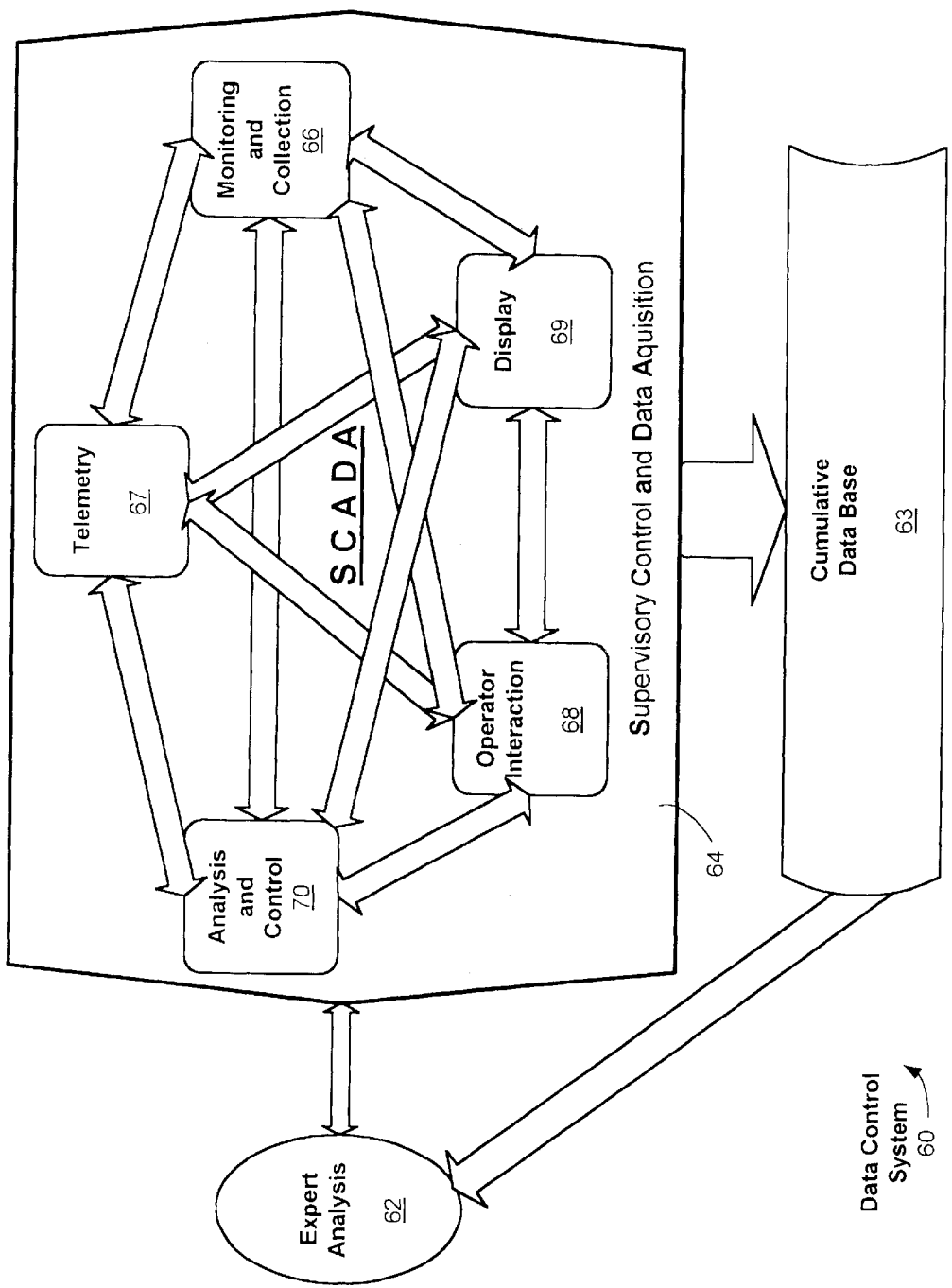
FIG. 5 is a schematic illustration of a SCADA portion of an embodiment of the present invention.

After the biomass materials of the solid feedstock 12 are received and weighed, large non-organic items are removed. Samples of incoming solid feedstock material are taken, analyzed and compared with prior samples as listed in the existing cumulative data base 63, as shown in FIG. 5. This expert data analysis 62, which can be performed off-site, then sends operational instructions to the local SCADA system 64. As shown in FIG. 3, the SCADA system sends instructions to pre-processing 17 that includes shredding, grinding, sizing, mixing, conditioning and supplementing the solid feedstock with the additives 18. Additionally, through pre-sampling and testing, data regarding the biological condition of each source is preferably established prior to allowing any biomass materials to be delivered to the site.

After only a brief operational period, the cumulative data base 63 will contain many solid feedstock sample results, all tested under laboratory conditions for potential bio-conversion into $CH_4$ and plant growth media. The biological condition of the source solid feedstock 12 is compared with the cumulative data base 63 for a match. From this material a formula is sent via the SCADA system 64 to the pre-processing 17 functions to select the correct method or methods to be employed. There are a large number of known additives 18 that can be injected at this point to assure that the "best" optimized silage results during the pre-processing and storage stage. Materials that may be added include anhydrous ammonia or dry ammonia nitrate for nitrogen balance, waste low-grade "sugars," sewage sludge's, animal wastes, food wastes, and liquid and solid wastes from food processing plants or municipal solid waste treatment plants.

FIG. 2 details these receiving, preprocessing and storage components 13. The analysis expert 62 of the solid feedstock 12 categorizes the solid feedstock. This analysis and categorization is used to determine the quantities and types of additives 18 in the preprocessing stage 17, as monitored by the SCADA system 64. After the comparison of the raw feed to an optimum feed has been determined, control and monitoring acquires the necessary information to control and monitor the pre-processing for optimal performance in the digesters 35, downstream. From here the SCADA system provides the necessary information to have the conditioned material placed in either a short term storage 22A, the long term storage 22B, or in a special storage 22C.

The special storage 22C is specifically for less stable materials or additives that typically "will not keep," or hold up under longer term storage conditions, such as fruit processing wastes. These materials can be kept in an oxygen free enclosed atmosphere to control odors and reduce further deterioration.

Once the solid feedstock 12 has been pre-treated in the pre-processing 17, it is moved to the appropriate storage 22. Typically, the pre-treated solid feedstock is moved into the long term storage 22B, which is most preferably a trench silo. The long term storage trench silo is preferably one of a parallel set of trench silos currently on line for filling. The solid feedstock is packed into the storage to remove air. An additional air removal system is also used at the storage step. The piping of exhaust gases with high $CO_2$ and little or no oxygen along the edges of the storage displaces the air in the storage atmosphere. The oxygen in the air, if not removed, can "spoil" or degrade the feedstock. When filled, the storage is preferably sealed to prevent oxygen from contacting the material.

A liquid feedstock 23 can also be utilized in the digester system of the present invention. The liquid feedstock can be any waste material that is free of toxic components. Examples of liquid feedstock can include waste water from food processing plants and liquid animal waste streams as typically produced by dairies. The liquid feedstock is preferably stored on site in a liquid storage 24, where it can be utilized as needed in the storage 22, to supplement the solid feedstock 12.

Preferably, many samples of the pre-processed material 20 from the storage 17 are taken over time with the SCADA system 64. Usually the pre-processed material converts into silage in approximately sixty to ninety days. The ensilaging process is self-regulating and stops when the pH reaches a sufficiently low, acidic level. The storage components 22 produce an ensilaged material 25 that can be safely stored for months or even years with little or no loss of quality. These samples are tested for bio-conversion in the next stage, which includes the anaerobic digesters 35.

The expert analysis results from these samples are sent to the cumulative data base 63, where the sample's bio-conversion ability is compared with previous samples and actual product results from the digesters 35. Over time, the cumulative data base will contain information from tens of millions of complete digester runs of biomass, from the source of the feedstock 12 through all stages of the process. Again it is the recent availability of adaptive, data mining software that allows this task to be economical, feasible and realistically implemented.

The SCADA system 64 also monitors conditions in the storage 22 components. This data is also compared with information in the cumulative base 63. A web of control connections 26 to the various components of the digester system 10 are utilized by the SCADA system. With the telemetered information from the SCADA system the PRS 65 is then used to identify patterns in the sets of conditions within the storage. These patterns may indicate that the ensilaged material 25 is ready for use in the digesters 35, or requires further aging.

It is this completing of both a feed forward and feedback control link, especially at this storage 22 stage, that allows the method of the present invention to obtain optimum results and utilize solid feedstock 12 and liquid feedstock 23 that make other digesters "sick." An ounce of prevention at an early stage is worth a "ton" of cure after the anaerobes get sick. As shown in FIG. 5 and detailed in FIG. 7, the expert analysis 62 performed by the data control system 60 in conjunction with the SCADA system 64, preferably employs the PRS 65 component. To illustrate a known example of biological pattern recognition, we can observe a human coming down with the flu. For this example, the patient could be throughly tested and closely monitored over time to compile a database of information. This information could include: blood chemistry, blood counts, medical history and biometric data. If sufficient patient data was available, both before and during the first twenty-four hours after exposure, it would be possible to recognize a "pattern of change, " which within hours would identify that the person has been exposed to a flu bug. Appropriate preventative action could begin immediately, instead of waiting the three to five days before the person "feels bad" and goes to a doctor to confirm they have the flu. It is this "early warning," pattern recognition, applied to the anaerobic digester system as exemplified by the present invention, that is at the heart of keeping the anaerobes working at optimum conditions.

The present invention also achieves end products that are consistent in quality. This product uniformity is largely due to the method of pre-treatment as part of the storage capacity of the digester system 10. The storage 22 and pretreatment allows materials to be held for months or even a year or more. The availability of large, low cost storage may improve the economics of a digester system plant in many locations, especially abandoned industrial sites. The storage is also utilized as a surge storage, allowing for seasonal fluctuations in the production of local bio-materials.

Formulating, Mixing and Control

A benefit of the digester system 10 process is that the preprocessing and storage components 13 makes the ensilaged feed 25 much more digestible, both in rate of conversion and total amount converted, as compared to the solid feedstock 12. The long dwell time in the trench silo of the long term storage 22B, allows woody and other hard to digest materials to be broken down. There are a number of additives 18, known to persons skilled in the digestion of wood products and the like, which when used with long exposure times of approximately six months and up to three years or more, can break down sawdust and other wood fibers into digestible materials.

The preprocessing and storage components 13, produce the ensilaged materials 25, in separate and metered streams, which allows these materials to be added in specific quantities to adjust the digester feed materials 31 to meet the desired "formula" to be fed to the digesters. This approach is similar to the alternative formulas used to feed cattle where each week or so during fattening. A somewhat different formula is used, which depends on the rate of weight gain observed in the cattle. In the digester system 10 approach of the present invention, the formula of the digester feed material is adjusted to keep the anaerobes at optimum rate of conversion. An expected initial sampling rate will likely include the collection of approximately five to ten samples per day for in depth analysis in the establishment of a base line.

Mixing and Transfer to the Digesters

A central objective of the digester system 10 of the present invention is to optimize the metabolism of the anaerobes within the digester 35. This optimization allows the use of the naturally occurring organisms at the plant site, no matter where on the planet the digester is located. Before designing for a specific site, local biomass with its associated anaerobes are identified and classified. The result is then used to establish the initial formula and environment for the anaerobic bacterial colony for start-up of the digester system 10.

Figure 7:
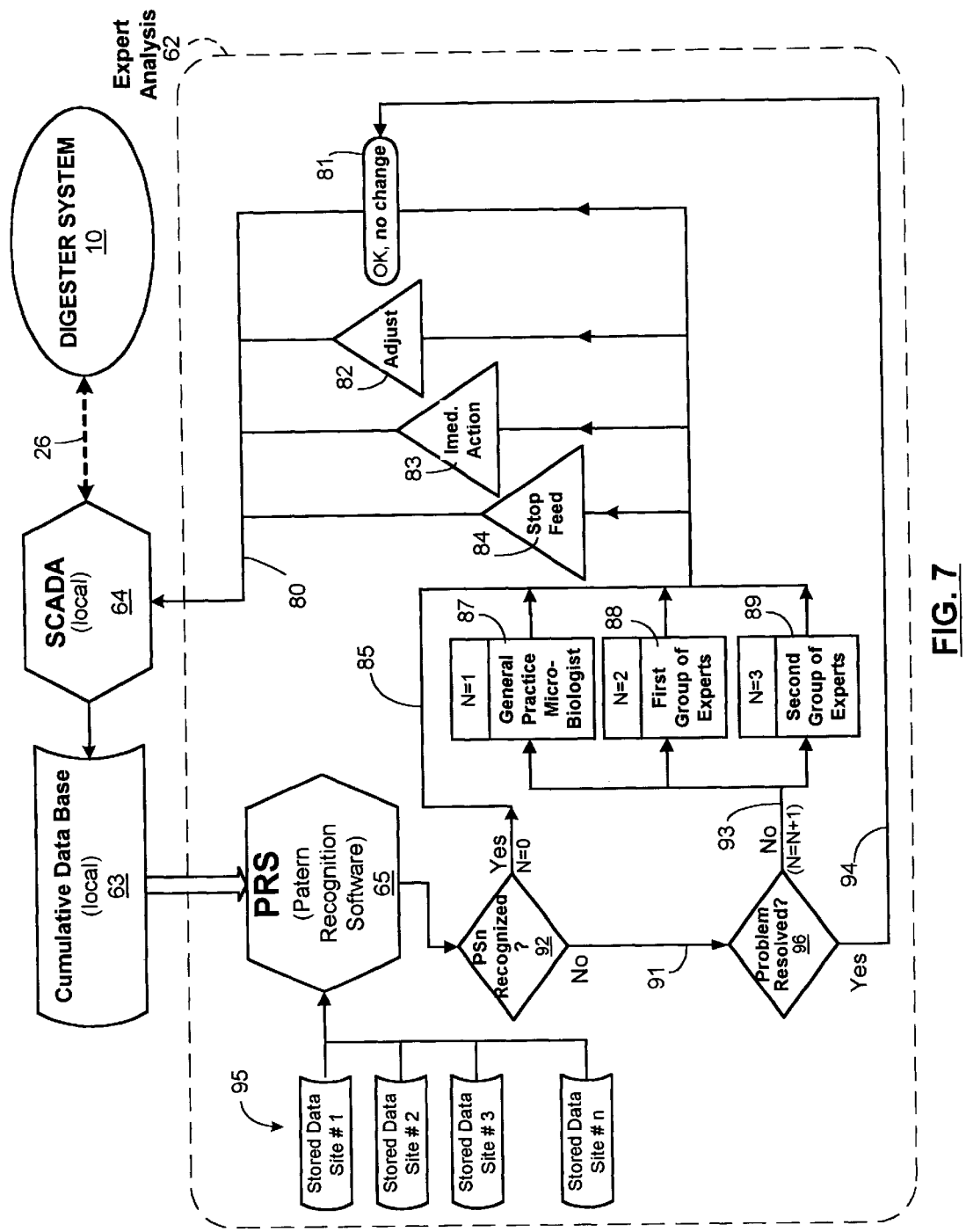
FIG. 7 is a schematic illustration of a digester system pattern recognition portion of an embodiment of the present invention.

Real time operating conditions from a set of local anaerobic digesters 35, as well as from many other units, are stored in the cumulative data base 63. Again, as shown in FIG. 7, the PRS 65 is utilized to compare actual conditions to desired, optimum and ideal or "first principle" conditions. It is the ability to control an operating digester as precisely as those under laboratory conditions that allow the digester system 10 approach to utilize first principles as the starting point for analysis. It is the use of these basic first principles that keeps the system from becoming "chaotic," which can happen when "neural networks" are used in an attempt to optimize biological systems.

As shown in FIG. 3, a number of different sources of ensilaged materials 25, most which have been preconditioned in the long term storage 22B of the trench silos are used to form the digester feed material 31, which is consistent and nearly in condition for introduction to the digesters 35. Each batch of digester feed material is mixed to a prescribed formula to be sure the feedstock meets the mutation rate of the "anaerobes" in each digester. The digester system 10 of the present invention is unique in its ability to accurately measure this rate of mutation or change.

Once the data analysis 62 function has identified what specific factors and values optimize the health of the anaerobes, the SCADA system 64 is able to adjust the digester feed material 31 to achieve the best possible start-up for the digesters 35. These factors can include very precise temperature control, a correct ratio of liquids to solids and a specific pH for the digester feed material. In addition, the SCADA system monitors for a uniform mixing, as performed by the mixer 32, so that each digester is receiving the same mixed silage 33 formula, under the same conditions. Thus, when differences are observed between digesters it follows that it is something within the digester instead of external. This is a key and essential factor in identification of what is required to keep the anaerobes healthy and metabolizing at their peak potential.

By the time the pre-processed material 20 is ready to be removed from the storage 22 its biological condition as it relates to the bio-conversion occurring in the operating digesters 35 is well known from information in the cumulative data base 63. As discussed above, certain additions, or silage additives 18, are available in liquid or solid form to adjust the feedstock from the storage to optimize the rate and quality of conversion in the digester.

Additional examples of silage additives 18 are limestone, ammonia nitrate and liquid wastes from local sources. The cumulative data base 63 also allows an economic discussion to be made about how much non-silage material can be utilized. An economic benefit can be realized from the fact the liquid wastes have a significant tipping fee for disposal. The reason this liquid can be processed is because the silage must be diluted with three to five parts water, preferably from a process water stream 28, to form a digester brew 56, which is shown within the digester 35 in FIG. 6. The digester brew is the mixed feed stream 33, preferably containing approximately 12% solids. This process water can include water from a variety of recycle and fresh sources. Preferably, as shown in FIG. 1, the process water is primarily from a liquid reuse storage 57, with the remainder needed provided by a make-up water 82.

As shown in FIG. 3, to best provide a consistent mixed digester feed stream 33, a weigh belt conveyor 27 is utilized to move the material from the metering bins 30 to the mixer 32. Associated with the weigh belt will preferably be a moisture meter to determine the actual amount of dry matter in the mixed silage stream. The metering bins can be of various sizes. One larger bin might hold approximately one hundred cubic yards of ground up gypsum dry wall material. The other bins will be of the same size or smaller and will be used for a large variety of materials.

The mass of all materials in the meter bins 30, as combined to produce the digester feed material 31 is determined by weigh belts 27 or metering pumps for liquid wastes. The amount of solids and moisture in the silage is known from samples taken during the time in storage 22 and associated pre-processing and storage components 13. The weigh belts from each metering bin, preferably feeds onto a common conveyor, which moves all of the material to the mixer 32.

The water stream 28 for diluting the digester feed material 31, or appropriate liquid, is preferably recycled from the de-water tank 42 and supplemented with the make-up water 82 and are both pre-heated to a temperature with the aid of a heat source 39. The temperature of the make-up water is preferably such that when mixed with cool solids will result in a mixed silage stream 33 of the correct temperature, which is approximately one hundred degrees F.

The mixer 32 is preferably a mixing station that contains a number of mixers, pumps or an alternative combination of mixers and pumps, which stir the digester feed material 31 to ensure a uniform consistency and temperature. It can require approximately four hours to fill the mixing chamber and have a uniform mixture ready to feed the digesters. There is preferably one pump to serve each digester. The feed rate to the digesters is determined from information accumulated in the cumulative data base 63. Ideally, the initial rate will be to feed at a rate that allows approximately thirty days retention time in the digesters. Information is accumulated and analyzed by the data analysis 62 operations. The pumping rate and time will be gradually increased until the maximum optimized rate is achieved for each of the different types of solid feedstock 12 sources of biomass.

Digesters

The storage, metering and mixing functions are followed by digesters 35 having a design built around maximizing anaerobic activity. With the introduction of process monitoring techniques that collect data on the on-going digestion process, the anaerobic digester system 10 improves the reliability of the anaerobic process. This is critical for use of the anaerobic digester system as a standard energy source, whether using the resultant methane directly as a combustible fuel or indirectly as a chemical source for methane-driven fuel cells. The monitoring is accomplished through the use of proven supervisory control and SCADA system 60 components, which are further discussed in a following section.

Again, the use of information technology allows the anaerobic digester system 10 of the present invention to increase the efficiency of methane production in both quality and quantity. Quality control is accomplished through the analysis of the SCADA system 60 acquired data and the execution of real-time adjustments to the digestion process. The present invention utilizes commercially available software and control applications, which are well known to those skilled in their respective fields of process control and data management. However, the present invention incorporates these diverse features together in a novel series of functional process steps, forming a system of expert analysis 62, which provides superior process control for the anaerobic digester system 10.

As shown in FIG. 4, an additional novel feature of the digesters 35 of the present invention is the gravity separation stage 34. This gravity separation is preferably performed as an integral component of the infeed 36 to the digester, but could be performed in a separate processing unit, as an alternative. The gravity separation removes everything heavier than water from the mixed silage infeed. The heavier materials 37, typically including primarily dirt and rocks, are removed and preferably cleaned with a wash water, and the wash water is then sent to the liquid reuse storage 57 for recycling. Any lighter inorganic material 38 that floats in the infeed are also automatically removed. Preferably a skimming system is employed to remove this lighter material, which is also cleaned with a wash water, and the water also reused. These separation processes allow the remaining biomass to be marketed as a high quality, plant growth medium after it is digested, thus eliminating further waste disposal issues.

An advantage of including the gravity separation stage 34 in the digesters 35 is that the gravity separation stage can utilize the digester vessel itself to further clean the mixed silage 31. Within the digesters, a drag chain bucket type device is preferably included to allow the removal of additional rock, dirt and other inorganic material. Preferably, an operator will watch the removed material as it passes over a trommel type of screen. At the start of the digester process, significant quantities of rock and dirt will likely pass out of the digesters and over the screen. Shortly after, the digester brew 56, which will flow through the digester, starts to emerge from the digester. The operator should stop this activity when the liquid digester brew component of the removed material reaches approximately 20%, by weight. Normally this process will be completed approximately once a week unless very dirty biomass is being used in the digester feed material stream 31. The removed material can be placed into large portable containers that will be dumped into a settling tank. Liquid from this tank will be preferably returned to the mixer 32. Inorganic material will be returned to the suppliers of biomass or disposed of in another appropriate manner.

Figure 6:
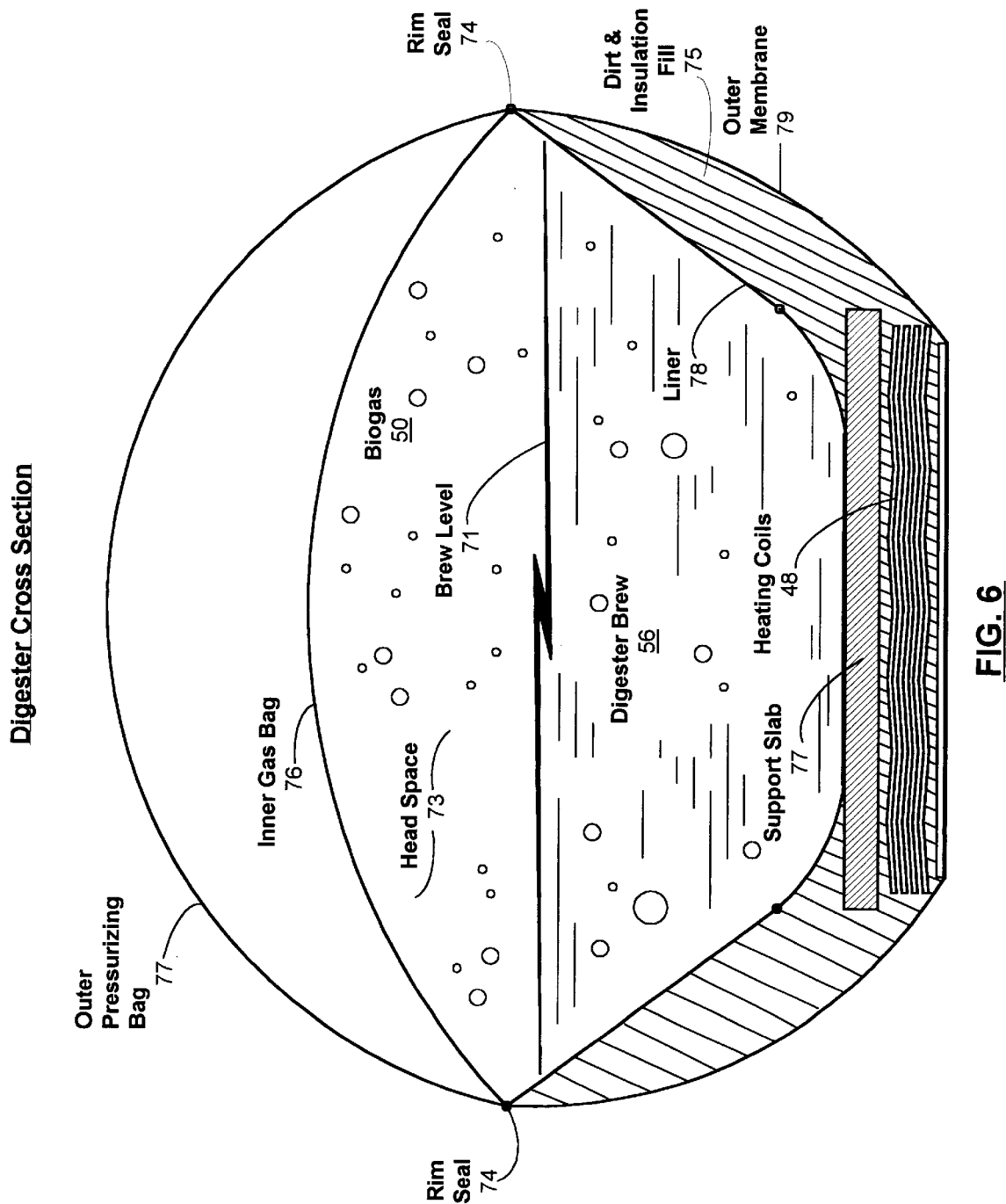
FIG. 6 is a schematic illustration of a digester cross section of an embodiment of the present invention.

In detailing the operation of the digesters 35, a variable speed pump 58 is employed to move the mixed digester feed stream 33 into the digester. The mixed digester feed stream preferably enters the digester at a center point slightly below a brew level 71, or surface of the digester brew 56, which are shown in FIG. 6.

There are a number of different naturally occurring anaerobic microorganisms in each digester 35. The kind and mix of microorganisms change from one end of the digester to the other. The end of the digester proximate the infeed 36 tends to have the anaerobes that produce acids, $CO_2$ and almost no methane. The microorganisms at the end of the digester proximate the exit 72 produces almost pure methane. Between the infeed and the exit of the digester, there is a gradual change in the mix of gases along the length of the digester. The digester system 10 of present invention includes a segmented gas collection system that utilizes materials with very small pores to preferentially remove certain desired gas products.

These small pored materials are sometimes called molecular sieves. One example, of a molecular sieve is GoreTex™, which allows vapor through but not liquid water. This is one of the types of material preferably employed in the present invention. It allows the collection of the condensed water with most of the dissolved $SO_2$. This can be much easier treated to convert the $SO_2$ into sulfur than treating the entire gas stream, which is the usual practice. There are other widely known materials, which selectively allow one gas over another to pass through. The segmented gas collection allows the incorporation of this approach. The result is that, instead of the normal 60% methane and 40% $CO_2$ gas mixture, by volume, the effluent has a much higher percentage of methane that can be collected with little, if any, increase in energy input to the process.

A result of this increased efficiency in the anaerobic digestion process 10, is that a portion of the gas to process stream 55 can approach pipeline quality, while the remainder, even though it may be low in heat content, as typically measured in British Thermal Units (BTU's), is a satisfactory by-product that can be used as an on-site or nearby energy source. For example, there are internal combustion engines that run on 100 $BTU/ft^3$ of "dirty gas." Such engines could readily handle the low BTU content gas by-product. The SCADA system 64, with associated sensors, as attached to the SCADA system through the control connections 26, allows this gas collection process to be automatic for optimization at each site. What is learned at one site can be shared with all other sites, so that improvements can be obtained that otherwise would not be possible.

Conventional digester systems utilize a gas tight bag over each digester. Wind, snow and other atmospheric conditions adversely affect the digester operation by deflecting or possibly collapsing the bag. A novel, lower cost approach as practiced in the present invention, allows a constant gas pressure to be maintained within the digester 35, while providing a gas containment that is more resistant to external environmental factors, as compared with conventional systems.

The digesters 35, as detailed in cross section in FIG. 6, produce a biogas 50 that is first collected in a head space 73 within the digester. The digester gases are compatible with conventional, air inflatable bags that are used with many commercial and industrial gas generating operations. Such an inner gas bag 76 preferably covers the entire digester, as shown FIG. 6. The inner gas bag is high tensile strength, and anchored to a rigid structure at a rim seal 74. The rim seal utilizes the weight of the digester brew 56 as weight to hold the inner gas bag in place. The inner gas bag preferably continues down into the digester to act as a liner and to provide anchoring, just as the outer pressurizing bag continues down beneath the digester to act as an outer membrane 79. A bag fitted to an industrial scaled digester can exert over a million pounds of upward thrust, when it is inflated to the desired gas operating pressure.

Between the liner 78 and the outer membrane 79, of the digester, a dirt and insulation fill 75 is preferably included. Also as preferred, the liner is supported at the bottom of the digester 35 by a support slab 77 that covers a series of heating coils 48 that supply the required heat 49 to the digester brew 56.

A pressurizing blower is preferably utilized to hold the outer pressurizing bag 77 at the desired gas discharge pressure. For safety and thermal considerations zero oxygen warm exhaust gases are used. The temperature can be adjusted so a warm air blanket covers the entire digester. Inside this exterior gas bag is the inner gas bag 76, which is a gas tight, flexible membrane. The inner gas bag seals the digester gas from the pressurizing outer bag. The digester 35, once up to operating condition, tends to produce biogas 50 at a constant rate. The inner bag can collapse down to the brew level 71 or expand nearly to the surface of the outer pressurizing outer bag. This head space 73 volume is available as surge capacity to maintain a constant gas pressure over a widely varying rate of use.

The SCADA system 64 adjusts the volume of inert gas between the outer pressurizing bag 77 and the inner gas bag 76 to maintain a constant pressure. This adjustment in turn keeps the same pressure on the gas side of this flexible, inner bag membrane. Since warm waste exhaust gases are generated, snow will melt as it falls, even in severe northern climates. Even if temporarily severe wind chills exists and ice forms on the inside of the external, outer pressurizing bag, the pressurized gas bag can be expected to hold up over twelve inches or more of frost, which is also an excellent insulation.

The methane gas stream 50 exiting the digesters 35 is warm and saturated with water vapor. The make-up water 82 is preferably employed in the process of the present invention to cool the gas stream and condense and move water along with the remaining $SO_2$. This allows all of the $SO_2$ to be treated as a dissolved liquid. This process is much easier and less costly than the process used to convert a low concentration of gaseous $SO_2$ into sulfur. All of the water condensed is returned to the process. As a result, not all of the $SO_2$ needs to be removed. In fact, 80% $SO_2$ removal is adequate, and greatly reduces energy use and waste.

The methane gas stream 50 is preferably collected from a number of different sections of the digesters 35. The nearly pure $CH_4$ from the exit end can be handled separately. This nearly pipeline quality "natural gas" can be sold to replace imported gas. For metallurgical purposes, this is pure $CH_4$ and is not mixed with other gases normally existing in pipeline quality natural gas. The methane produced is ideal for any application that requires a substantially pure methane stream. Fuel cells and small turbines are prime examples of such applications.

De-watering Digested Brew

The mash 40, of digested brew is pumped out the exit 72 of each digester with a pump 82 at a nearly constant rate. This allows a simple belt type de-watering press to be used. AU of the water is sent to a large storage tank, where it can be used for the "next day's" mixing of digester feed material 31. The water from the dewatering process will be a mix from all of the digesters. It will then be stored in one large tank for liquid reuse storage 57.

The now de-watered "plant growth media" (PGM) mash 40 has very low "biological oxygen demand" (BOD), and "chemical oxygen demand" (COD). After the mash is de-watered 42, it proceeds to the screen 44 for the removal of any remaining oversized or undigested materials, and to improve product consistency. The screen can be any conventional material processing screen, such as preferred, a shaker type trommel screen, or a rotary screen as an alternative. The de-watered and screened mash is passed to the storage and packaging stage 46, where a solid product 90, which is an inert, high-grade potting soil that is ready to be packaged and delivered to an end user.

As noted above, different formulas are used to adjust the solid product 90 for different end user needs. Since the digester removes only carbon, all of the plant nutrients remain. Because of the naturally occurring pre-treatment and digester microorganisms, the original feedstock hasbeen greatly enhanced from a plant growth media perspective.

The process of the present invention creates a plant growth media solid product 90 that has all of the qualities of a combination of sphagnum peat moss, and a powerful plant food along with beneficial enzymes, a product that is not currently available in the commercial market place.

Supervisory Control and Data Acquisition

As first discussed above, the digester system of the present invention utilizes the SCADA system 60 to optimize the operation of the anaerobic digester process. The SCADA system of the present invention control employs data acquisition technologies from the chemical industry and additionally includes data analysis techniques from the biological sciences to identify cause of process problems and effect corrective actions. This improved system is made possible with "pattern recognition" techniques embodied in computer based programs that are known in the art of data management and analysis. One such PRS 65 program that meets the requirements of the present invention is found in "Knowledge Discovery Solutions™" (KDS™) software, as manufactured by SRA International, Inc. of Fairfax, Va. These types of intelligent, "data mining" programs go beyond conventional analytical processing and decision support systems typically employed for process monitoring and control in industrial chemical processes. These data mining algorithms efficiently discover patterns in historical data to accurately predict and effect desired process outcomes.

The SCADA system 64 of the present invention is referred to as supervisory in that the system interacts with the process to manage it for the purpose of attaining the desired process outcomes. The term supervisory data control and acquisition is shortened to SCADA to refer to this complex but effective group of interconnected functions that oversee, or supervises the anaerobic digester system.

The data control system 60 is detailed in FIG. 5. The monitoring and collection functions 66, include probes positioned throughout the process to monitor all relevant environmental parameters (e.g., temperature, pH levels, and pressure) within the anaerobic digester system 10. The present invention utilizes off the shelf software algorithms to analyze this data, as it is compiled over time. This historical, cumulative data is employed to generate operational adjustments to ensure that the process is continually optimized and operating at peak efficiencies. The operational data and the monitored results of any adjustments are captured through telemetry 67 and stored in a cumulative database 63. These databases can then be analyzed by an expert, PRS 65 system, such as the KDS™ analytical expert software. The historical data is typically far too voluminous to be interpreted by conventional statistical methods. As a part of the expert analysis functions 62, the expert analysis includes software that mines the historical data for such information as trends, cause and effects, critical variables and process sensitivities. Over time, this data mining function evolves, to provide ever more repeatable and optimal process results.

During the first months or even years of operation of the first few anaerobic digester system plants, a significant amount of necessary baseline measurements and analysis will need to be established. Once this is done, it is expected that the amount of data acquired can be reduced substantially. The data monitoring and collection functions can be reduced over time as a direct result of the expert analysis tool. Superfluous data, or at least the non-critical measurements can be discarded or suspended, thereby significantly reducing the volume of data collected and the start-up and operational costs of future plants.

The following are the expected minimum amount of measurements and analysis needed for each different solid feedstocks, taken at the receive, weigh and separate functions 14, schematically shown in FIGS. 1 and 2. All data should be correlated back to the original source and how it has been processed, to the degree that this is possible.

Continuous measurements of the solid feedstock 12 should include moisture content in order to establish mass of dry matter, measurements of the weight of material per unit of volume, the temperature of the solid feedstock material, and the pH of the material.

Additionally, a large number of samples of the solid feedstock will be taken for analysis by on-line instruments, site laboratory instruments, and by off site labs, as required. Examples of these samples could include pH, nitrogen content, screening for volatile organic compounds (VOC's), organic acid analysis, biodegradable components, checks for toxins or radio isotopes, if suspected, inorganic breakdowns, BOD and COD. Total carbon and general assays of total soluble and insoluble components would also be of use.

The production anaerobic digester system 10 will also be utilized for a considerable amount of research relating to anaerobic digestion. Some or maybe all of them will have a large number of ports for taking samples. These initially may be taken manually with potential future automation. Each digester 35 will be equipped to accept a fill compliment of sensors, all connected to the SCADA system 64 by the web of control connections 26. Some digesters will have all of the sensors installed, while other digesters may have fewer sensors initially installed. It is essential that the sensor location and sample ports be identified at the first design step. Each subsequent step must be examined to assure there will be no interference with their proper function.

There are a number of unique physical features of the present invention that allow the production digesters 35 to be maintained at conditions very close to a chosen set point. In fact the precision of control closely approximates that obtained in a typical laboratory. Mass flows, energy input and output, temperatures, pH, density and gas production, which is tied directly to the metabolic rate of the microbes, can be closely monitored with the system of the present invention. As shown schematically in FIG. 5, the cumulative database 63 exchanges data within the SCADA system 64. Preferably this data exchange is achieved with a telemetry function 67, which can provide high-speed connections with the fastest possible interaction between the various components of the SCADA system, including operator 68 and display 69 functions.

Another function of the SCADA system 64 is analysis and control 70. The analysis and control functions are firstly conventional and constrained by simple set points, as typically found in industrial applications. The analysis and control function includes common feed back controls, but as a secondary function and a novel improvement, the analysis and control is overridden by the process control input from the expert analysis 62. The expert analysis functions are external to the SCADA system, but within the data control system 60 of the present invention. Without the external expert analysis function, the analysis and control of the SCADA system can only respond in a reflexive, feedback mode. The expert analysis provides a predictive, feed forward control of the anaerobic digester system 10, with its intelligent, pattern recognition features.

The SCADA system 64 is an adept tool for recognizing incremental changes in measured parameters that fall outside of normal, set point ranges. The relationship of the physical aspects of the monitoring and collection 66 features of the SCADA system, as employed in the present invention, are designed in a manner that would assure that a high level of analysis and control 70, preferably in the parts per million range for most monitored parameters. This high degree of precision is accomplished using "off the shelf" hardware, but in a novel manner, as discussed herein. There is a term used in control systems called signal "noise." As used here it means the error in a measurement signal or in the ability to control at a desired set point due to extraneous signals. If the level of noise is a significant percentage of the phenomena that needs to be measured or monitored then mostly "garbage," or an erroneous and grossly inaccurate reading shows up as a monitored output signal, making effective control impossible.

For the digester system 10, the primary phenomena that must be precisely measured is the metabolic rate of the anaerobes within the digesters 35. To achieve the required precision in measurement, the physical design of the digesters must depart from conventional designs. The digester design of the present invention begins with a highly insulated shell that reduces the heat input required to maintain a given temperature by a factor often to fifty times over typical "plug-flow" type anaerobic digesters. This super-insulated shell is augmented by "a primary heat exchange method," which reduces the energy needs, by another factor often to twenty times. The result is the ability to measure and control to a precision where the "signal noise" is now no more than 50% of the metabolic rate of the anaerobes. With the digester's thermal characteristics, monitored as temperature and under such precise control, the other physical parameters, such as mass flow, heat input or output, pH, density and gas production, all can also be measured at levels that are one hundred or more times more precise than typical plug flow anaerobic digesters. The precise monitoring and maintenance of temperature corresponds to a reduction in the "noise level" within the digesters to a level that is well below the level necessary to precisely measure the "health" of the anaerobes.

Another element in the control strategy of the present invention is to bring each digester 35 to an inactivated, steady state and hold it for an extended period of time. Inactivated describes a condition of the digester when there is no anaerobic activity within it. This can be achieved by effectively sterilizing the contents of the fully charged digester to halt all anaerobic activity. The monitored data from the inactivated digesters is employed as the "base line" against which any future changes are compared in the operational digesters. Because over 99% of the thermal energy input is utilized to maintain steady state conditions, by using this base-line approach only 1% of the thermal energy flow has to be known to a high precision. The result is the ability to identify changes in thermal energy input to one part per million. As stated above, this reduces the "noise" level below that which is required to identify the metabolic rate of the anaerobes.

Now that the background noise, which is essentially the non-metabolic phenomena within the digesters 35, has been reduced below the level of the desired signals to be monitored, the digesters can be efficiently monitored and controlled to a high degree of precision. There are a large number of useful microorganism related measurements that can be made. Some include the dissolved gases and fluid chemistry, similar to those tested in blood analysis. Others include the rate of bacterial mutations similar to those used in medical assay cultures, which also precisely determine the number and type of microorganisms per unit volume.

This incremental control strategy is conventionally called the "guarded hot plate" approach. As shown in FIG. 6, there is a bank of pipes, or heating coils 48 that act as heat exchangers and circulate hot water, preferably distributed around the outside of the membrane holding the digester brew 56, which is also mostly water. The temperature of the circulated water in the pipes is adjusted such that there is no heat flux, or heat exchange, across the surface of the liner 78. As noted later in the description of thermocouple (thermopiles), it is easy to measure a temperature difference of 0.01 degree F. At this small of a difference, it would take over a thousand hours to change the temperature of the digester brew 56 only a single degree F.

Under these conditions the small amount of energy required to maintain a specific temperature in the digester chamber can be measured quite accurately. Instead of hundreds of thousand or even millions of BTU's an hour in conventional plug flow digesters, the digester system 10 approach of the present invention requires only approximately one thousand BTU's an hour to maintain a precisely constant temperature, even in cold climates. A heat flow measurement of 0.1% is a reasonable measurement accuracy and equal to approximately one BTU, for a single digester. In many conventional digesters, the heat flow measurement error can be over one thousand BTU's. The metabolic rates of the anaerobes have a low thermal output. At a level of one BTU precision in heat flow for a digester it is possible to identify a change in the metabolic rate of the anaerobes. Metabolic rate is directly related to activity and health. This is another place where pattern recognition, as facilitated by the PRS 65 will allow the identification of optimum conditions.

Thermocouples (TC's) have been made for more than one hundred years. This old and maybe forgotten thermal measurement technique is preferably employed to the unique thermal properties of the anaerobic digester system 10 of the present invention. Thermocouples measure temperature difference between the hot end, or variable measurement, and the cold end or fixed, ice point. Certain types of thermocouples are used in secondary standard temperature measurements. Even high-grade thermocouples will have an error of 1%, which corresponds to an error of one degree F. at one hundred degrees F.

If a thermocouple were to be used to measure the temperature of the digester brew 56 in the present invention, the uncertainty would be two degrees F. However, the information needed is how much, if at all, the digester brew has changed in temperature. The same TC that has an accuracy of 1% has a repeatability of better than 0.001 of a degree F. This is because TCs have one thousand times better accuracy in measuring temperature differences in that in the measurement of values. In addition, thermocouples can be connected in a serial manner called a "thermopile" so that a signal generated by the temperature differential can be multiplied by a factor of ten, twenty or even one hundred, or more. For the SCADA system 64, the present invention preferably utilizes a twenty element thermopile to obtain a signal approximately twenty thousand times that of a single high grade thermocouples. There are other types of precision temperature measurement that are accurate to 0.01 degree F. but are more expensive, often by a factor often times or more. Since the SCADA system 60 may use hundreds of temperature measurements, cost is a major factor. This same thermopile arrangement is used in the "guarded hot plate" thermal barrier approach to protect the digester 35 from variations in outside temperatures.

There are currently available relatively low cost automated methods of performing these various measurements. Projected across the length and depth of each digester, tens of thousands of data points can be produced every few minutes if they are needed that often. Analysis of these million plus data points per digester per day would normally be considered too costly. However, the present invention provides a solution to this problem.

The actual amount of data to be analyzed grows arithmetically with the number of digesters in operation that employ the anaerobic digester system of the present invention. The possible number of variations in formulation of the digester feed 31 grows exceptionally as different solid feed stocks 12, and liquid feed stocks 15, are utilized. After a few years, it is easily conceivable, given the great need for a biomass processing system, that a thousand to ten thousand anaerobic digester plants, all employing the SCADA system 64 features of the present invention, could be operational. Each plant would include several digesters 35, and these digesters would be fed, at one geographic location or another, easily over one hundred different types of biomass. The enormous amount of data generated by these systems could not have been considered for analysis prior to this invention.

The naturally occurring anaerobic microorganisms in the digester system 10 will produce many generations per day. These varieties of anaerobes have survived for hundreds of million of years, by adapting through mutation to changing feed stocks and environmental conditions. This can be both a benefit to analysis and a serious drawback. A key to the anaerobic digester system of the present invention is the ability to "mine" information from all the data gathered from all the digesters of any anaerobic digester system for the entire length of time they have been in operation. This lifetime of operation is estimated to be typically ten to fifteen years, or longer.

Digester System Pattern Recognition

FIG. 7 shows a schematic of the pattern recognition processes employed in the digester system 10 of the present invention. At start-up, each of the twenty or more anaerobic microorganisms within the start-up batch will have stabilized under a constant set of conditions. Preferably, each distinct variety of anaerobe has been assessed and cataloged employing a serial number, or another appropriate method of identification. This assessment can be made from the examination of a small sample of the digester brew 56 by a technician that is qualified as a microbiologist, employing standard sampling and laboratory techniques.

The populations of the various anaerobes and the conditions monitored in the digester 35 are a data set that can be viewed as a pattern, and stored as a standard pattern "set" (PSs), in the cumulative data base 63. The KDD™, or alternative equivalent of the PRS 65, then compares each subsequent, non-pattern set (PSn) of data to this standard, PSs set.

The expert analysis 62, as shown schematically in FIGS. 5 and 7, preferably includes analysis by one of the world-class experts in anaerobic microorganisms. These experts, from anywhere in the world, will provided a range of conditions over which specific anaerobic microorganisms, of which they are knowledgeable, are considered still healthy. These conditions can also be stored as ideal pattern sets (PSi), and compared, by the PRS 65, to any particular PSn or PSs. The cumulative data base 63 contains this information and makes it available to the PRS 65 for comparisons of minimum, hourly, daily operating conditions to the acceptable range for those parameters. The PRS then feeds back, to the cumulative data base, the appropriate analysis set in the form of the PSn, to be sent to a "general practitioner" (GP) 84. This GP may be on site, or at a remote site. There may be only a single GP or there may be several GP's in a round-table group or in a network of consultants. The GP's first look at these flagged patterns to determine if they have the knowledge to make formula changes, or they may select one or more of the off site experts, or another GP to review the data and patterns.

The expert analysis 62 functions of the present invention controls a microbiological process, and bears a close resemblance to the digestive system controls of large herbivores. These large herbivores survive by employing internal, biological systems that maintain health, instead of only responding to sickness. The analysis process for the present invention employs this same approach, responding to patterns of data that if left unchecked, historically resulted in reduced biogas 50 production from the digesters 35. The expert analysis 62 function of the present invention can often recognize a correctable pattern of data from the digester system 10 and resolve the problem without additional expert input.

There are four possible actions by the expert analysis 62 function. The actions are directed along an output path 80, which directs the SCADA system 64, through the control connections 26, to control and further monitor the digester system 10 in the specified manner.

An "O.K., no change" response 81 by the expert analysis 62, is appropriate when the recognized data pattern PSn function 92 elicits no change in process control. This response requests that the digester system 10 be left as is, and that the monitored process is O.K. and proceeding within acceptable norms of operation.

An "adjust" response 82 is appropriate when an adjustment is required of the digester system 10 to essentially maintain the health of the anaerobes. The adjust response requires the SCADA system 64 to implement a "fine tuning" type of control response. If this response is not effective, or the recognized data pattern PSn function 92 requires a harsh, or vigorous adjustment, an "immediate action" response 83 is executed. The precise action taken by the SCADA system 64 is included in the immediate action response, the instructions for the response are based upon the historical responses and results as mined from the PRS 65. Preferably, the immediate action response also notifies the site operator and the GP of the suspected problem and the decisive correction.

If the actions of the SCADA system 64, as instructed by the expert analysis 62 have failed to produce the desired corrective results or the digester system is in an emergency condition, the expert analysis can require a "stop feed" 84, to halt further processing and thereby minimize damage to the digester system 10. This allows the process to be examined by the experts and the process corrected and brought back online, while the SCADA system monitors the corrections and stores the series of problem conditions and corrective measures taken, for future use by the expert analysis system.

When the PSn, as mined by the PRS 65, is a pattern that includes a pre associated response, the PSn recognized "Yes" path 85 is followed. The expert analysis 62 instructs the SCADA system 64 to execute one of the four commands as associated with the known data pattern.

If the PSn, as mined by the PRS 65, is not a pattern that is recognized as resolvable, the expert analysis 62 function proceeds along a PSn recognized "No" path 91 to a "problem Resolved?" 96 decision function. At the problem resolved function, if the PSn has an associated "problem," meaning an out of tolerance condition or a monitored trend that requires preventative correction, the program proceeds to the problem resolved "No" path 93. If there is no problem associated with the PSn, the PSn is stored and the problem resolved "Yes" path 94 is followed to the OK, no change 81 process instruction. All patterns mined by the PRS 65 are preferably stored in a series of stored data banks 95. These stored data banks archive all patterns, as well as fixes and results for each digester system 10, which employs the process of the present invention. This archival data is very helpful in providing additional pattern recognition and resultant corrective commands for the expert analysis.

To aid in the implementation of the expert analysis 62, the PSn can be assigned a response index integer "N." If the PSn is recognized as paired with a known solution to the problem, the index N is set to zero and the prescribed response is given on the PSn recognized "Yes" path 85. However, if the problem was not resolved, and the program proceeds on the problem resolved "No" path 93, the index is preferably increased by an integer step of one and the program proceeds to the appropriate "expert" that matches the value of the index. With the stepped increase in the integer value, the expert analysis follows a series of iterations that interpret the PSn by experts of increasing skill and knowledge. For a first iteration, the index is one and the PSn is referred to the GP 87. The responses available to the GP are again the same four available to all decision function and includes OK 81, adjust 82, immediate action 83 and stop feed 84.

This problem, as observed by the PRS 65 is relatable to predicted or realized anaerobic health, as directly monitored in the production rate of biogas 50 from the digesters 35. If the GP response is inadequate, or the nature of the problem received a higher response index than zero, the problem resolved "No" path 93 increases the response index integer to the next higher value and additional experts are consulted. The experts are ranked in order of cost and availability to the system in that simpler problems should be easily diagnosed by sources of general knowledge. For the preferred example, as detailed in FIG. 7, the GP 87 is a first expert that is preferably a general practitioner of microbiology, since the response index is one for the GP, it is the first level of evaluation when an "out of tolerance" condition occurs.

Once the operational tolerances are established, there is an initial set of acceptable conditions that is provided by the appropriate "world class experts," to the SCADA system 64, which can begin to monitor for these conditions. Within the "stored data" for each site is the comparative software for looking at the data as it is generated by the site's SCADA system. The GP 87 then uses the analytical tools previously provided by the "world class experts" to determine a course of action to which there are the same four response possibilities.

The higher response indexes of two and three, call for a "referral" to one or more "World class experts" who has a specialty in the apparent "disease" or problem as discovered by the PRS 81. These experts may function in an analogous way to an oncologist who specializes in a particular type of cancer in humans. The oncologist can look at seemingly abstract patterns in x-rays for that particular disease, just as the first and second group of experts specialize in diagnosing and treating particular problems in anaerobic digestion.

A first group of experts 88, can include one or more world class experts. The experts are preferably persons having strong backgrounds in anaerobe biology, however these experts could conceivably be computer based systems that embody the knowledge of an expert or body of experts. The first experts are sent the data and appropriate patterns from the large, cumulative database 63 and PRS 65, along with the specific formulas being used. They have the same four possible process responses.

In some cases, the PSn needs additional analysis by another specialist and the response index is increased to three. This is when a second group of experts 89 may be utilized. The second group can also include one or more experts, preferably of a "world class," and with even greater or uniquely specialized expertise in anaerobe microbiology. This need for additional consultation by the second group may occur when a really strange and very rare thing happens to the microorganisms.

To effectively apply PRS 65 to these large numbers and varieties of anaerobic digester systems 10 that are potentially included in the system of the present invention, there are a number of iterative steps that can be taken. A first step is the identification of existing laboratory data banks and anaerobe "experts." Secondly, data banks 95 to be utilized by the PRS in identification of "patterns" must be selected. An Intranet is preferably established and protocol adopted for telemetering information exchanges between the various anaerobic digester systems and the expert analysis 62 system of the present invention employed.

The PRS 65 program must have the ability to first receive digester system data 95 from operating digesters 35. Then, the pattern recognition software must adapt to look for comparisons between operating digester data with clinical data from anaerobe laboratories and other "expert" resources. Potential pattern "matches" are then compiled and sent to the selected experts for analysis. The potential pattern matches, PSn, are compared with the changes in physical parameters for one or all-operating digesters. At this point, cause and effect relationships will begin to emerge. Now the formulas and/or operating conditions in the digester system can be changed. As a result, the expert system will be able to send updated formulas and operational parameters to the SCADA system 64 located at each anaerobic digester system 10 site. The system can learn cause and effect relationships by comparing the predicted responses of the systems versus actual results.

After the digester system 10 has been running and achieved steady state operation, useful data can be obtained. Each digester 35 has measurements that are preferably taken at approximately every five feet along the length of the digester, so that there are twenty or more zones of data for each digester. There are a number of unique physical features of the digester system that allows the digester vessel to be maintained at conditions very close to a chosen set point. In fact the precision of control is equal to that obtained in a typical laboratory. Mass flows, energy input and output, temperatures, pH, density and gas production, which is directly related to the metabolic rate of the anaerobes, are the main parameters to be monitored.

In a first zone, the input of approximately one hundred data points or samples are preferably taken and transmitted to the data warehouse. This data is simultaneously compared by the local SCADA system 64 to the previous steady state data. All changes outside preset limits are flagged and transmitted to the expert analysis 62 function. The PRS 65 of the expert analysis queries the data storage 95: "Has happened before? If so, what adjustments were required?" Based on the results of this query, the expert analysis program can proceed to take the same action that was successful in the prior instance, as fundamentally detailed in FIG. 7 and discussed above.

The same thing occurs for zone two, the next five foot of cross sectional area of the digester 35. In this case, zone two now knows that within approximately twenty-four hours the feed from zone one will have changed to the new conditions. Each zone has the ability to have a number of different materials injected, preferably in small amounts, to adjust conditions to meet the optimum needs of the specific anaerobes that are alive and "working" in that section of the digester at that time.

The unique method of insulation and thermal control allows "laboratory" type measurements to be made in each of the digester system's 10 operating production digesters 35. This results in parts per million changes in the microorganisms to be able to be identified. In microbiology it is said, "an ounce of prevention is worth a pound of cure." This is more than true in the anaerobic digestion process of the present invention. A very small amount of buffer material, a basic "antacid," material, can correct a pH unbalance when it first starts to occur in one section. After the entire digester gets a "stomach ache," it may take very large amounts of material and days to return the system to health. In some cases the contents must be removed and discarded. Returning to full production can require one to two months to properly pre-process the solid feedstock 12.

Probably, and now in the predicative scheme of feed forward control, a more significant fact is that a small change in temperature may have been what caused the pH imbalance. Therefore, a temperature adjustment is what the expert analysis 62 will require, not adding a buffing material to correct an apparent low or high pH. This cause versus effect is actually very complex. For example, if zone two is operating near maximum and providing zone three with a high rate of a given mixture, and then zone two receives less feed from zone one and starts to slow down and/or go into upset conditions, then almost all of the corrective action needs to occur in zone one, which is actually causing the problem in zone three.

Additional, continuous monitoring of the digester 35 would also include liquid level, density at depth versus pressure on bottom of digester, temperature, pH and the gases being released. The fermentation industry, specializing in beer, cheese, wine, and pharmaceuticals, routinely perform simple and low cost tests, typically in a lab environment, to test how well the fermentation process is going. The anaerobic digesters of the present invention may be more correctly called "fermentation chambers." The present invention preferably employs automated test methods borrowed from the fermentation industry to monitor the metabolism of the anaerobes.

Also, in the digester system 10 of the present invention, small representative samples of the material in the preprocessing and storage components 13 are collected. The representative samples are then mixed with the culture from each of the operating digesters 35 for the time periods of approximately two weeks, one week and one day prior to being used as digester feed material 31. The data provided through the analysis of these samples allows the formula in the mixer 32 to be adjusted to optimize the digester process. The expert analysis 62 functions compare the data from the lab and to the subsequent data from each digester. Pattern recognition techniques are used to identify trends, as well as cause and effect relationships. This in turn allows for future adjustments in the formula used in the mixer 32.

Some literature references suggest that there are at least twenty different types of anaerobes in a typical operating plug flow digester 35, like those used by the digester system 10 of the present invention. Because these microorganisms change and mutate fairly quickly, typically in the span of a few hours, it is difficult to identify what organisms exist at various points in a digester at any one point in time.

The field of medical technology has developed automated culture methods that allow quick and low cost identification and cataloging of microorganisms. These technologies will be adapted to the digester system 10 of the present invention. The anaerobe identification data becomes part of the data control system 60 and is specifically stored in the cumulative data base 63. This anaerobe data can then be accessed and mined by the expert analysis 62, which employs the data mining capabilities of the PRS 65 system. Again, it is the potential patterns of the massive amount of data, which provides information to optimize the process of the present invention.

The SCADA system 64 of the present invention can employ data warehousing of the stored data 95 to archive the vast pool of data necessary for analysts to properly diagnose problems that may arise with biogas producing anaerobic digestion. The expert analysis 62, especially the functions of the GP 87, the first group of experts 88, and the second group of experts 89, will likely each find improvements for processing of the solid feedstock 12 and perhaps design modifications to the digester system 10.

The approach of the present invention departs from the more conventional implementation of a data warehouse facility. Data warehouses are usually employed in the re-engineering of corporations. As such, they receive their data from a preexisting operational environment, which is generating that data on a fairly constant basis. Frequently, archival data from that environment is not incorporated into the data warehouse. There is a host of problems associated with extracting data from an operational environment to be archived in a data warehouse. Many of these problems stem from the fact that the different systems in the operational environment treat data differently from each other and from the database management systems (DBMS) which are used as the engine for such data warehouses.

Although the design of a data warehouse must be accomplished intuitively, since the analysts do not know what they are looking for beforehand, a great deal of the conventionally encountered difficulties can be eliminated in an environment that builds both operational and data warehouse programs simultaneously.

The most essential aspect of creating an operational and data warehousing environment is to use the same programing for both. Simply utilizing an expert analysis 62 that employs the same DBMS and creates unique keys for data, which can go into the warehoused data storage 95 without modification, will go a long way toward resolving some of the thornier programming difficulties associated with transferring data from the operational to the warehouse environment.

For the digester system 10 of the present invention, it will be crucial to determine the best means to store the large volumes of data anticipated in the project. Because of the time required to access data in a sequential environment, it may be preferable to use newer optical disk storage methods for archiving of data.

A preliminary assessment of the production environment for the projects employing the digester system 10 of the present invention indicates that a large volume of data will be flowing from the operational facilities to the Intranet server(s). The initial system must have the ability to grow into a very large worldwide Information Management System (IMS) that is capable of receiving, analyzing and delivering updated information to thousands of locations and possibly hundreds of thousands of people.

In compliance with the statutes, the invention has been described in language more or less specific as to structural features and process steps. While this invention is susceptible to embodiment in different forms, the specification illustrates preferred embodiments of the invention with the understanding that the present disclosure is to be considered an exemplification of the principles of the invention, and the disclosure is not intended to limit the invention to the particular embodiments described. Those with ordinary skill in the art will appreciate that other embodiments and variations of the invention are possible, which employ the same inventive concepts as described above. Therefore, the invention is not to be limited except by the following claims, as appropriately interpreted in accordance with the doctrine of equivalents.

The following is claimed:

1. A method for controlling an anaerobic digester system comprising the steps of:
   a) storing a feedstock to form a digester feed material, the feedstock substantially comprised of a biologically generated component,
   b) digesting the digester feed material in a digester, to form a biogas and a digested material;
   c) monitoring and collecting a plurality of digester datum from the digester,
   d) telemetering the plurality of digester datum to a cumulative data base; and
   e) mining the cumulative data base to compile a predictive, feed forward control of an anaerobic digester system, the anaerobic digester system including the digester.

2. The method for controlling an anaerobic digester system of claim 1, further comprising the step of:

f) recovering the biogas generated within the digester with a biogas recovery system.

3. The method for controlling an anaerobic digester system of claim 1, further comprising the steps of:

f) storing the feedstock in a storage chamber to pre-treat the digester feed material; and g) monitoring and collecting a plurality of storage datum from the storage chamber, h) telemetering the plurality of storage datum to the cumulative data base; and i) mining the cumulative data base for a predictive, feed forward control of the anaerobic digester system, the anaerobic digester system additionally including the storage chamber.

4. The method for controlling an anaerobic digester system of claim 3, further including the step of:

j) mining the cumulative data base to compile a reflexive, feed back control of the anaerobic digester system.

5. The method for controlling an anaerobic digester system of claim 1, further including the steps of:

f) measuring metabolic activity within the digester; and g) including a metabolic activity datum in the plurality of digester datum telemetered to the cumulative data base.

6. The method for controlling an anaerobic digester system of claim 5, further including the steps of:

h) mining the cumulative database for a feedstock correlation, the feedstock correlation including a relation of a feedstock formula with respect to the metabolic activity datum; and i) utilizing the feedstock correlation in a feed forward control for adjusting the feedstock formula to optimize anaerobic production activity.

7. The method for controlling an anaerobic digester system of claim 6, further including the step of:

j) utilizing the feedstock formula correlation in a feed back control for adjusting the feedstock formula to optimize anaerobic production activity.

8. The method for controlling an anaerobic digester system of claim 5, further including the step of:

h) mining the cumulative data base to compile a reflexive, feed back control of the anaerobic digester system.

9. The method for controlling an anaerobic digester system of claim 1, further including the step of:

f) mining the cumulative data base to compile a reflexive, feed back control of the anaerobic digester system.

* * * * *